United States Patent
Kilyanek et al.

(10) Patent No.: US 10,843,178 B2
(45) Date of Patent: Nov. 24, 2020

(54) N-HETEROCYCLIC CARBENE (NHC) BASED LIGANDS AND RELATED METHODS

(71) Applicant: The Board of Trustees of the University of Arkansas, Little Rock, AR (US)

(72) Inventors: Stefan M. Kilyanek, Fayetteville, AR (US); Rajesh Thapa, Fayetteville, AR (US)

(73) Assignee: The Board of Trustees of the University of Arkansas, Little Rock, AR (US)

( * ) Notice: Subject to any disclaimer, the term of this patent is extended or adjusted under 35 U.S.C. 154(b) by 194 days.

(21) Appl. No.: 16/105,532

(22) Filed: Aug. 20, 2018

(65) Prior Publication Data

US 2019/0054455 A1 Feb. 21, 2019

Related U.S. Application Data

(60) Provisional application No. 62/547,253, filed on Aug. 18, 2017.

(51) Int. Cl.
*B01J 31/22* (2006.01)
*C07D 403/12* (2006.01)

(52) U.S. Cl.
CPC ........ *B01J 31/2273* (2013.01); *C07D 403/12* (2013.01); *B01J 2231/4211* (2013.01); *B01J 2231/4261* (2013.01); *B01J 2531/008* (2013.01); *B01J 2531/0238* (2013.01); *B01J 2531/17* (2013.01); *B01J 2531/824* (2013.01); *B01J 2531/847* (2013.01); *B01J 2540/40* (2013.01)

(58) Field of Classification Search
None
See application file for complete search history.

(56) References Cited

PUBLICATIONS

Hazari et al., Organometallics, 30, 1818-1829 (Year: 2011).*

* cited by examiner

*Primary Examiner* — Yun Qian
(74) *Attorney, Agent, or Firm* — J. Clinton Wimbish; Nexsen Pruet, PLLC

(57) ABSTRACT

Polydentate macrocyclic NHCs (NHC ligands) and related methods are disclosed. Such ligands advantageously facilitate a variety of ligand coordination modes and stabilize oxidation states of metal complexes with a number of coordination environments and shapes. The NHC ligands described herein comprise pendant groups configured to facilitate a variety of reactions including: cis-trans isomerization, proton shuttling and facilitating changes in coordination environments as a result of redox reactions.

6 Claims, 6 Drawing Sheets

Imidazole (3a)
Benimidazole (3b)

Table 1.

| Entry | Substrate | Catalyst | Time (h) | Yield[a] |
|---|---|---|---|---|
| 1. | 4-bromonitrobenzene | 5a | 3 | 100 |
| 2. | 4-bromonitrobenzene | 5b | 3 | 100 |
| 3. | Bromobenzene | 5a | 3 | 61 |
| 4. | Bromobenzene | 5b | 3 | 50 |
| 5. | Bromobenzene | 5a | 6 | 96 |
| 6. | 4-iodoanisole | 5a | 16 | 96 |
| 7. | 4-iodoanisole | 5b | 10 | 100 |
| 8. | 4-bromotoluene | 5a | 3 | 97 |
| 9. | 4-bromotoluene | 5b | 3 | 70 |
| 10. | 4-chlorotoluene | 5a | 24 | 37 |
| 11. | 4-chlorotoluene | 5b | 24 | 9 |
| 12. | 4-chloroacetophenone | 5a | 8 | 52 |
| 13. | 4-chloroacetophenone | 5b | 8 | 100 |
| 14. | 4-chloroacetophenone | 5a | 17 | 70 |
| 15. | 4-bromoacetophenone | 5a | 3 | 100 |
| 16. | 4-bromoacetophenone | 5b | 3 | 100 |
| 17. | 4-bromotoluene | 5a | 7 | 64[b] |
| 18. | 4-bromonitrobenzene | 5b | 7 | 9[b] |
| 19. | 4-bromonitrobenzene | 5a | 7 | 4[b] |

[a]The average of two runs determined by H NMR using an internal standard. No increase in yield was observed if the reaction was left for longer period of time. Condition: all reactions used 1 mol % of PdC, $Cs_2CO_3$ (0.90 mmol), substrate (0.20 mmol), phenylboronic acid (0.45 mmol) and 1,4-dioxane (1.5 mL) at 100 °C under $N_2$. [b]Catalyst loading: 0.1 mol%

FIG. 5

Table 2.

| Entry | Catalyst | Cat. mol % | Time (h) | Yield (%)[a] | TOF[b] |
|---|---|---|---|---|---|
| 1 | 5a | 0.1 | 1 | 50 | 510 |
| 2. | 5a | 0.1 | 1.5 | 60 | 400 |
| 3. | 5a | 0.1 | 4 | 70 | 670 |
| 4. | 5a | 0.02 | 1 | 38 | 2037 |
| 5. | 5b | 0.1 | 1 | 66 | 660 |
| 6. | 5b | 0.1 | 1.5 | 85 | 567 |
| 7. | 5b | 0.1 | 4 | 82 | 1025 |
| 8. | 5b | 0.02 | 1 | 46 | 2378 |

[a]Yield determined by H NMR using an internal standard (1,3,5-Trimethoxybenzene), only trans isomer was observed. [b]Turnover frequency (TOF) = (mol of product)/((mol of Pd).h). Condition: Reactions used 0.1 and 0.02 mol % of catalyst 5a and 5b, aryl halide (0.2 mmol), $Na_2CO_3$ (0.24 mmol), tetra-n-butylammonium bromide (0.02 mmol), n-butyl acrylate (0.4 mmol, 2 equivalent), dimethylacetamide (1.5 mL), 140 °C

FIG. 7B

Table 3.

| Entry | Substrate | Cat. mol. % | Time(h) | Yield | Selec. |
|---|---|---|---|---|---|
| 1. | 4-bromonitrobenzene | 0.1 | 4 | 100 | trans |
| 2. | 4-bromoacetophenone | 0.1 | 1 | 51 | trans |
| 3. | 4-bromoacetophenone | 0.02 | 1 | 32 | trans |
| 4. | Bromotoluene | 0.1 | 7 | 47 | trans |
| 5. | Bromobenzene | 0.1 | 8 | 42 | trans |
| 6. | 4-iodoanisole | 0.1 | 1 | 65 | trans |
| 7. | 4-chlorotoluene | 0.1 | 16 | 0 | — |
| 8. | 4-chloroacetophenone | 0.1 | 16 | 0 | — |

[a]Yield determined by H NMR using an internal standard (1,3,5-Trimethoxybenzene); only trans isomer was observed. Condition: reactions used 0.1 and 0.02 mol % of catalyst 5b, aryl halide (0.2 mmol), $Na_2CO_3$ (0.24 mmol), tetra-n-butylammonium bromide (0.02 mmol), n-butyl acrylate (0.4 mmol, 2 equivalent), dimethylacetamide (1.5 mL), 140 °C.

FIG. 7C

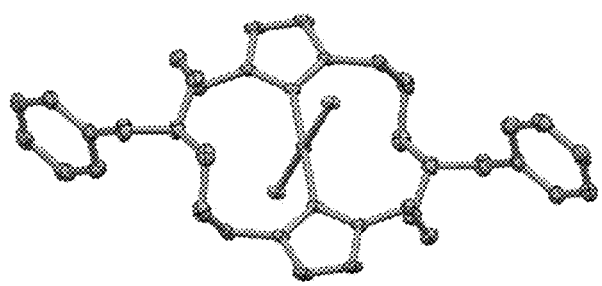
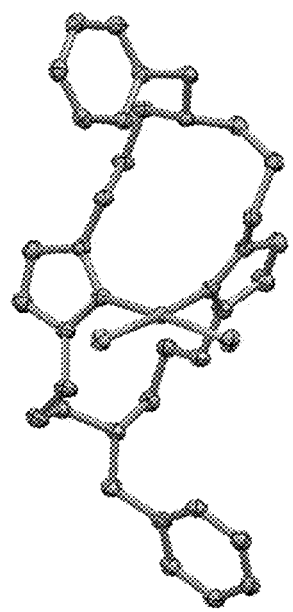
6a-*trans* ligand
6a-*cis* ligand
FIG. 7D

N-HETEROCYCLIC CARBENE (NHC) BASED LIGANDS AND RELATED METHODS

RELATED APPLICATION DATA

The present application claims priority pursuant to 35 U.S.C. § 119(e) to U.S. Provisional Patent Application Ser. No. 62/547,253 filed Aug. 18, 2017 which is incorporated herein by reference in its entirety.

BACKGROUND

N-heterocyclic carbenes (NHCs) are ubiquitous ligands often used to support a variety of metal environments for catalysis. However, existing NHCs have limited scopes and lifetimes. It is challenging to obtain catalysts that can be reliably employed in industrial processes.

Accordingly, a need exists for improved NHC ligands (macrocycles) and related methods.

BRIEF DESCRIPTION OF THE DRAWINGS

FIG. 5 is a table of data obtained for reactions employing NHC based macrocycle ligand catalyst according to an embodiment of the subject matter herein.

FIGS. 7B-7C are tabularized data obtained for reactions employing NHC based ligand catalysts according to an embodiment of the subject matter herein.

FIG. 7D is a schematic diagram of a Ni(NHC) ligand according to an embodiment of the subject matter herein.

DETAILED DESCRIPTION

Figure 1:
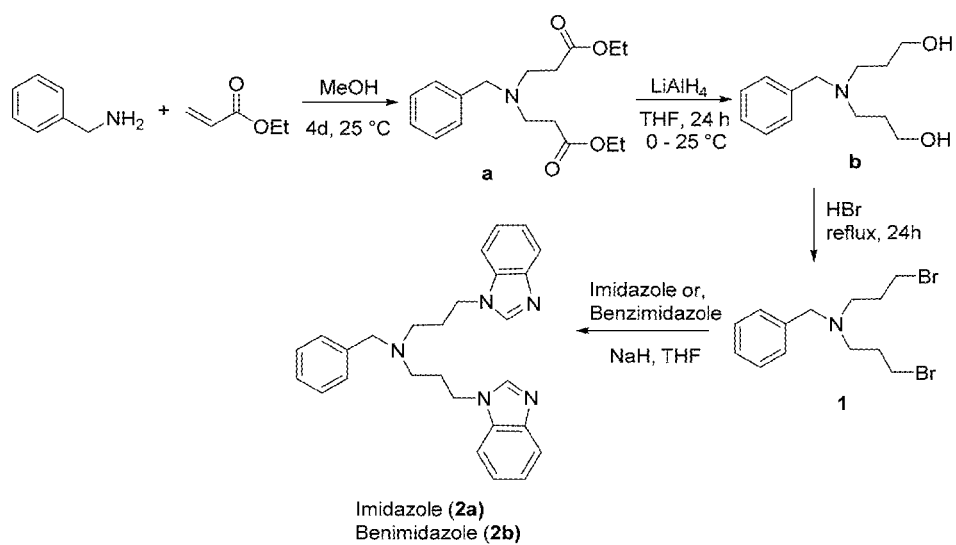
FIG. 1 is a schematic diagram of synthesizing NHC based ligand precursors according to an embodiment of the subject matter herein.

Polydentate macrocyclic NHCs (NHC ligands) and related methods are disclosed. Such ligands advantageously facilitate a variety of ligand coordination modes and stabilize oxidation states of metal complexes with a number of coordination environments and shapes. The NHC ligands described herein comprise pendant groups configured to facilitate a variety of reactions including: cis-trans isomerization, proton shuttling and facilitating changes in coordination environments as a result of redox reactions. Such ligands are highly flexible (non-rigid) and, thus, not kinetically trapped by formation of stable ring conformers that prevent molecular fluxionality. Accordingly, the NHC based ligands described herein can coordinate of a variety of transition metals including the 3d, 4d, and/or 5d metals.

Further, the NHC based ligands set forth herein are valuable as supports for catalysts for a variety of organic transformations such as, for example, C—C, C—H, and C—N coupling reactions, hydrogenation reactions, and any other reduction/oxidation reactions not inconsistent with the objects of the instant disclosure. As described in more detail below, the disclosed ligands are also employed for stabilizing platinum (Pt) group metals, which are commercially useful for a large number of catalytic transformations.

I. NHC Based Ligands

According to one aspect, NHC based ligands are described herein. Such ligands comprise cis- or trans-isomers of the compound of formula (I) below, or a salt thereof.

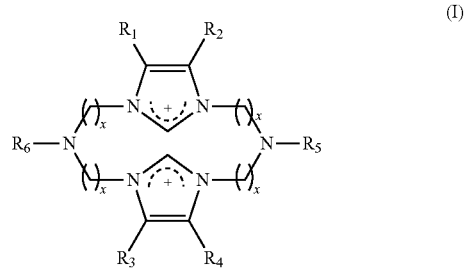

(I)

Briefly, in Formula (I) above $R_1$ and $R_2$ are each, individually, hydrogen, a substituted or unsubstituted C1 to C10 hydrocarbyl group, or $R_1$ and $R_2$ together form a saturated or unsaturated C1 to C10 ring. Further, $R_3$ and $R_4$ are each, individually, hydrogen, a substituted or unsubstituted C1 to C10 hydrocarbyl group, or $R_1$ and $R_2$ together form a saturated or unsaturated C1 to C10 ring. $R_5$ and $R_6$ are substituted or unsubstituted C1 to C10 hydrocarbyl groups and x is an integer from 1 to 6. As used herein, the terms "cis" and "trans" refer to the relationship of $NR_5$ and $NR_6$.

In some embodiments, $R_1$, $R_2$, $R_3$, and $R_4$ are each individually hydrogen, and form compound according to Formula (II) below.

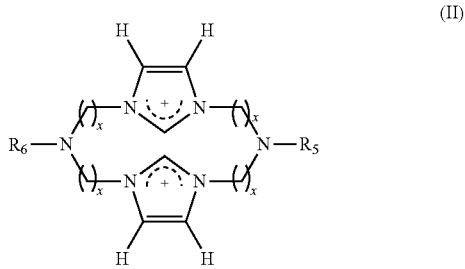

(II)

In further embodiments, $R_1$ and $R_2$ together form a phenyl ring and $R_3$ and $R_4$ together form a phenyl ring forming a compound of Formula (III) below.

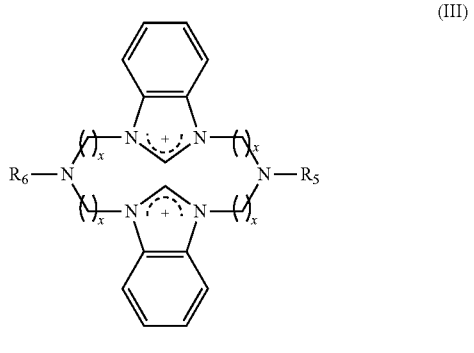

(III)

In any of Formulas (I), (II), and (III) described above, x can be 1, 2, 3, 4, 5, or 5. In some embodiments, $R_5$ and $R_6$ are both methyl benzene. In yet further embodiments, the ligands comprise a salt of Formulas (I), (II), and/or (III), such as a halide salt.

Notably, the NHC based macrocycle complexes having formulas (I), (II), and (III) contain both amines and NHCs. These highly fluxional macrocyclic ligands facilitate the formation of stable NHC-metal complexes having a unique steric environment. The NHC based macrocycle complexes described herein complexes are also active for C—C bond forming (i.e., coupling) reactions.

A variety of alkyl groups can also be incorporated into the synthesized ligands and attached to the amine nitrogen groups, in some embodiments. Additionally, the size of the ligand can be synthesized. This can allow for a variety of steric and electronic environments that will influence the catalytic activity of the noble metal complexes.

The NCH ligands described herein are flexible (non-rigid) and highly fluxional macrocyclic ligands allowing for cis or trans isomers. Notably, the NHC ligands described herein can chelate (coordinate) 3d, 4d, and 5d transition metals. Additionally, such ligands are polydentate, and therefore form more stable complexes. Polydentate complexes, such as the NCH ligand complexes, comprise multiple coordination sites acting as multiple "teeth" which bite or attach to a transition metal center. Notably, the NCH ligands according to the formulas above can attach to a metal atom in more than one place and are less likely to fall off the metal center, which results in the formation form more stable compounds. The stability of these compounds is such that they exist under a variety of reaction conditions and temperatures. In catalysts, polydentate ligands lead to more stable catalysts that remain reactive for a larger number of chemical reactions. Reactions including hydrogenation, C—C, C—N and C—H coupling reactions have applicability for this ligand class.

NHC ligands according to the formulas above are effective pre-catalysts for organic transformations and find applicability in a variety of reactions. Such ligands advantageously result in a variety of steric and electronic environments.

II. Methods Employing NHC Based Ligands as Catalysts

According to a further aspect, methods of reacting compounds are disclosed; such methods are performed in the presence of a NHC ligand comprising a composition according to any of Formulas (I), (II), and/or (III) described in Section I above.

Briefly, a method of reacting a compound having Formula (XI) and a compound of Formula (XII) in the presence of a catalyst of Formula (I), (II), or (III) is provided.

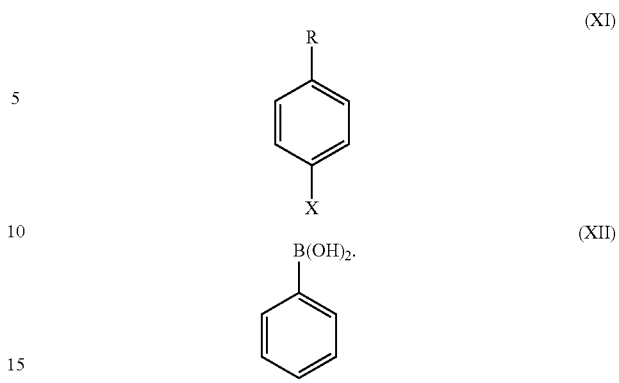

(XI)

(XII)

In Formulas (XI) and (XII) above, X is selected from the group consisting of Cl, Br, and I and R is selected from the group consisting of H, $CH_3$, —$COCH_3$, —$OCH_3$, and —$NO_2$. In certain embodiments, Formula (XII) is 4-bromonitrobenzene, 4-iodanisole, bromotoluene, 4-chlorotoluene, bromobenzene, chlomoacetophenone, 4-bromoacetophenone, 4-bromotoluene, or 4-bromonitrobenzene.

The NHC ligands can be used to coordinate Pd complexes, Ag complexes, Pt complexes, Ni complexes, Ru complexes, Re complexes, Ir complexes, or any other complex formed from a 3d, 4d, or 5d transition metal not inconsistent with the objects of the instant disclosure. The reaction times can vary from 1-50 hours or any subrange thereof (e.g., 1-30 hours, 5-25 hours, 5-20 hours, 8-10 hours, etc.)

In certain embodiments, the reaction product formed using the NHC ligands described herein are a compound of Formula (XIII) and the yield is greater than 50%.

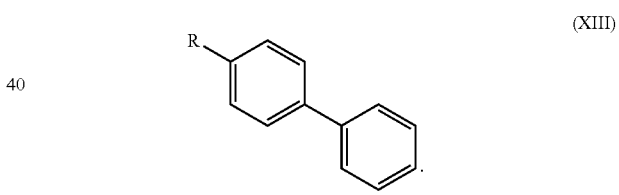

(XIII)

In formula (XIII) above, R is selected from the group consisting of H, $CH_3$, —$COCH_3$, —$OCH_3$, and —$NO_2$.

Some non-limiting examples regarding the instant subject matter are provided below. Numerous modifications and adaptations will be readily apparent to those of skill in the art without departing from the instant disclosure.

EXAMPLES

NHC Based Macrocycle Synthesis

FIG. 1 is a schematic illustration of a synthesis reaction for providing NHC based macrocycle precursors. Referring to FIG. 1, bis(ester) (a) is synthesized from commercially available benzylamine and ethyl acrylate through a Michael addition reaction. Reduction of the bis(ester) (a) with $LiAlH_4$ produces bis(alcohol) (b), which is converted into the bis(bromide) (1) by refluxing with a 48% aqueous solution of HBr for 24 hours.

N-benzylbis(3-bromopropyl)amine 1 (FIG. 1) is obtained via refluxing N-benzylbis(3-bromopropyl)-alcohol with excess 48% HBr for 24 hours. N-benzylbis(3-bromopropyl) imidazole (2a, FIG. 1) and N-benzylbis(3-bromopropyl)

benzimidazole (2b, FIG. 1) are obtained via reacting N-benzylbis(3-bromopropyl)amine 1 (FIG. 1), sodium hydride, and imidazole or benzimidazole in THF solvent respectively as seen in FIG. 1. Both compounds 2a-b are colorless viscous liquids.

Figure 2:
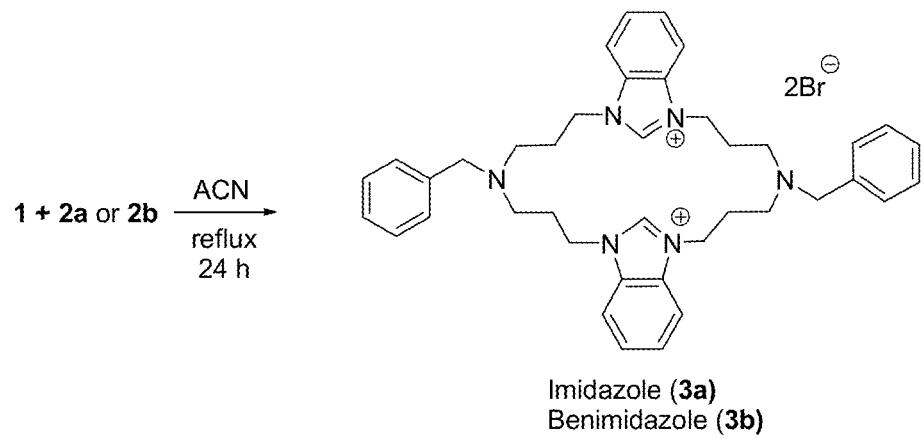
FIG. 2 is a schematic diagram of synthesizing NHC based ligands according to an embodiment of the subject matter herein.

FIG. 2 is a schematic illustration of a synthesis reaction providing NHC based (cyclic bisimidazolium bromide salt) macrocycles 3a and 3b. A condensation reaction between N-benzylbis(3-bromopropyl)amine 1 (FIG. 1) and N-benzylbis(3-bromopropyl)imidazole 2a (FIG. 1) or N-benzylbis(3-bromopropyl)benzimidazole 2b (FIG. 1) yielded the corresponding cyclophane-like 20 membered cyclic bisimidazolium bromide salts 3a-b as seen in FIG. 2. The saturated chloroform solution of 3a was precipitated as a white solid at −40° C. The bisbenzimidazolium bromide salt 3b was precipitated as a white solid from a saturated acetonitrile solution of 3b at −40° C.

High-resolution ESI mass spectrum of the NHC based macrocycle ligand in 3a showed peaks at 591, 593 m/z that corresponded to $[C_{32}H_{44}N_6Br]^+$ and 511 m/z for $[C_{32}H_{44}N_6]^+$. Similarly, the NHC based macrycycle ligand in 3b showed peaks at 691.3118, 693 m/z that corresponds to $[M-Br]^+$. A crystal suitable for X-ray crystallography of 3a was obtained by slow diffusion of chloroform into a solution of 3a in dichloromethane. The X-ray diffraction analysis of $C_{34}H_{44}N_6 \cdot 2(CHCl_3)$, 3a confirmed the conclusion drawn from the nuclear magnetic resonance (NMR) and mass spectra.

Figure 3:
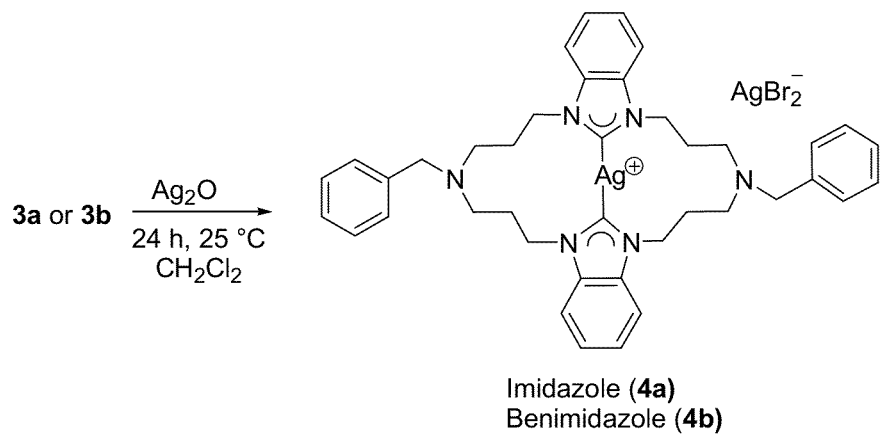
FIG. 3 is a schematic diagram of synthesizing Ag(NHC) ligands according to an embodiment of the subject matter herein.

FIG. 3 illustrates conversion of imidazolium salts 3a-3b to silver (I) bromide complexes 4a-4b that can subsequently act as ligand transfer agents to palladium. The reaction of imidazolium salt 3a-3b with two equivalents of $Ag_2O$ in methylene chloride at room temperature under a nitrogen atmosphere in the absence of light yielded analytically pure, light-sensitive silver carbene complexes 4a-4b in high yields as white crystalline solids.

Synthesis of Pd Complexes

Figure 4:
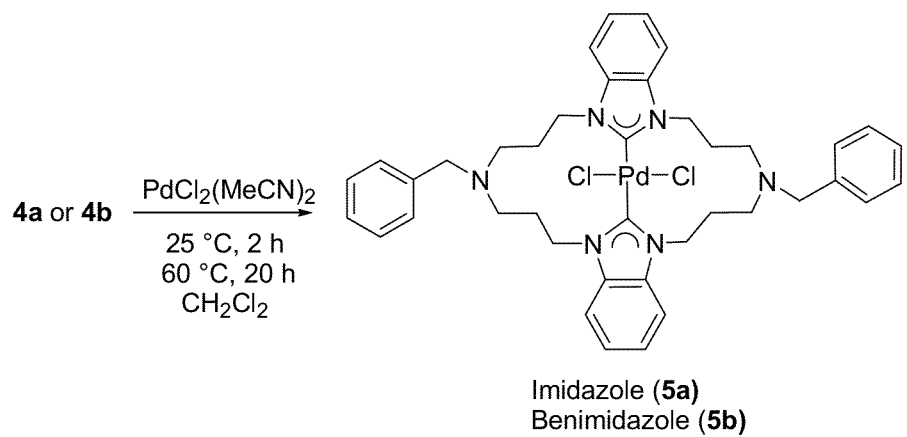
FIG. 4 is a schematic diagram of synthesizing Pd(NHC) ligands according to an embodiment of the subject matter herein.

FIG. 4 schematically illustrates transmetalation of the Ag(I)NHC based macrocycle complex formed in FIG. 3 using bis(acetonitrile)dichloropalladium(II) $[PdCl_2(MeCN)_2]$. The palladium complexes 5a-5b in FIG. 4 were prepared via the reaction of Ag(I)NHC complexes 4a-4b with $PdCl_2(MeCN)_2$. The reaction between Ag(I) NHC complexes and $PdCl_2(MeCN)_2$ results in the immediate formation of the characteristic pale yellow silver bromide precipitate.

The silver bromide suspension was separated by filtration through celite, the volatile impurities were removed by evaporation under vacuo, and the resulting solid was washed with diethyl ether to give a white solid in 60% yield. The solid state structure determined by single x-ray diffraction analysis show only one conformation that is trans Pdbis (NHC) with square planar geometry at the Pd center The trans-$[PdCl_2(bis(NHC))]$ complexes 5a-5b synthesized in FIG. 4 are stable in air and moisture. The $^{13}C$ NMR signals attributed to the carbene carbon were observed at 170.7 and 170.5 ppm for complex 5a and at 180 and 182 ppm for complex 5b in $CD_2Cl_2$ and are comparable to the chemical shifts observed in other trans Pd(NHC) complexes.

Pd—NHC Complex Catalyzed Suzuki Coupling Reaction

Figure 6:
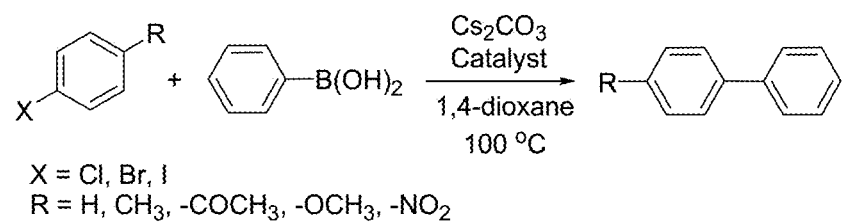
FIG. 6 is a schematic diagram of Suzuki coupling of aryl halide with phenylboronic acid employing a NHC based ligand according to an embodiment of the subject matter herein.

The trans-$[PdCl_2(bis(NHC))]$ complexes 5a-5b (FIG. 4) were analyzed for Heck and Suzuki cross-coupling carbon-carbon bond forming reactions. The yields are in Table 1 shown in FIG. 5. The Suzuki reaction i.e., coupling of aryl halide with phenylboronic acid, is a widely known cross-coupling reaction. FIG. 6 is a schematic illustration of the Suzuki reaction of coupling aryl halides with phenlboronic acid using a PdC (5a-5b) catalyst, as palladium-based catalysts are generally employed to promote this reaction. The trans-bis(NHC)Pd(II)$Cl_2$ complexes 5a and 5b (FIG. 4) were investigated for their catalytic activities towards the Suzuki coupling reaction of various aryl halides with phenylboronic acid. The reaction conditions for the Heck and Suzuki couplings are provided hereinbelow.

The product of the Heck and Suzuki reactions was detected using gas chromatography/mass spectroscopy (GC/MS) and the percentage yield was calculated from a comparison of the proton resonance of the product to the known proton resonance of an internal standard compound (1,3,5-trimethoxybenzene). A stock solution of 5a (0.04 Molar) was prepared in dichloromethane. 50 μL (1 mol %) stock solution of trans-$[PdCl_2(bis(NHC))]$ complex 5a was injected in the reaction mixture. The reaction was conducted in 1,4 dioxane in the presence of $Cs_2CO_3$ as the base at 100° C. under low catalyst loadings of 1 mol % and 0.1 mol %.

In FIG. 6, the Suzuki coupling of aryl halide with phenylboronic acid was catalyzed by 1 mol % of palladium complexes. As FIG. 5 indicates, the bidentate trans-bis(NHC)Pd(II)$Cl_2$ complexes 5a and 5b are active catalysts for the Suzuki and Heck cross coupling reactions. However, trans-bis(NHC)Pd(II)$Cl_2$ complex 5a has a wide range of yields, ranging from moderate to an excellent yield for the Suzuki-Miyaura coupling reaction. Complex 5a is an active catalyst for the Suzuki-Miyaura coupling reaction. Various aryl halides including aryl chlorides, bromides and iodides were coupled with phenylboronic acid in good to excellent yields (Table 1, FIG. 5). The less reactive substrate 4-chloroacetophenone coupled with phenylboronic acid 100% with 1 mol % catalyst 5b in 8 hours (entry 13, Table 1, FIG. 5). 4-bromotoluene (entry 6, Table 1) and 4-bromonitrobenzene (entry 1, Table 1) are highly active substrates in the Suzuki-Miyaura coupling reaction.

Due to the quantitative coupling of aryl bromides using catalysts 5a-5b, the coupling of 4-nitrobenzene and 4-bromotoluene with phenylboronic acid was selected for further investigations at a lower catalyst loading (0.1 mol %). At 0.1 mol. % catalyst use, 4-bromotoluene was found to be active.

Ni—NHC Complex Catalyzed Heck Coupling Reaction

Figure 7A:
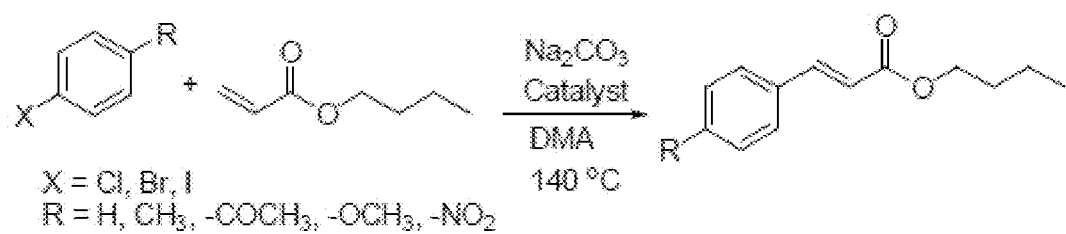
FIG. 7A is a schematic diagram of a coupling reaction employing a NHC based ligand catalyst according to an embodiment of the subject matter herein.

FIG. 7A is a schematic illustration of a Heck coupling reaction using a PdC (5a-5b) catalyst. FIGS. 7B-7C are data tables indicating yields obtained from such reactions. Treatment of 4a (FIG. 3) with NiCl$_2$(PPh$_3$)$_2$ in refluxing CH$_2$Cl$_2$ yields 6a, depicted in FIG. 7D in moderate yield (60%, 100 mg scale). The complex 6a in FIG. 7D is observed to be a mixture of isomers by NMR. Crystallization of 6a in different environments yields single crystals of the cis and trans isomers (both depicted in FIG. 7D). In the presence of adventitious water, the cis compound is isolated. In the absence of water (e.g., glovebox conditions) the trans isomer is exclusively isolated.

Pd—NHC Complex Catalyzed Heck Coupling.

The Heck coupling reaction with 0.1 mol % of catalyst 5b, 4-bromonitrobenzene and 4-bromoacetophenone shows high yields and trans selectivity. 4-bromobenzene is comparatively sluggish compared to 4-bromoacetophenone, but still gave a moderate yield at longer reaction times using 0.1 mol % catalyst 5b. 4-bromoacetophenone showed a yield of 32% using 0.02 mol % catalyst 5b, which is a good yield. 4-chlorotoluene does not show any reactivity and 4-chloroacetophenone shows low reactivity with 0.1 mol % of catalyst 5b. Catalysts 5a-5b demonstrated excellent and improved catalytic performance compared to existing catalysts.

General Procedure for the Suzuki Coupling Reactions

A 15 mL pressure tube with stir bar was charged with 4-bromoacetophenone (31 mg, 0.2 mmol), phenylboronic acid (36 mg, 0.45 mmol), cesium carbonate (196 mg, 0.90 mmol) and 1,3,5-trimethoxybenzene (20-30 mg). Then 1,4-dioxane (1.50 mL) and solution of the catalyst in DCM (0.1 mol %, 50 µL, 0.04 M) was added. The reaction mixture was heated to 100° C. in an oil bath with vigorous stirring. The solution was allowed to stir, after which time it was analyzed by gas chromatography (GC) and $^1$H NMR.

General Procedure for the Heck Coupling Reactions

A 15 mL pressure tube with a magnetic stirrer bar was charged with aryl halide (0.20 mmol), n-butyl acrylate (51.3 mg, 0.40 mmol), n-butyl ammonium bromide (6.5 mg, 0.02 mmol) and 1,3,5-trimethoxybenzene (20-30 mg). A solution of the Pd(NHC) complex (0.02 mol %, 50 µL, 4 mM solution) in methylene chloride was added. Anhydrous $Na_2CO_3$ (24 mg, 0.23 mmol) and N,N-dimethylacetamide (2 mL) were added. The reaction mixture was submerged in an oil bath at 140° C. The solution was allowed to stir, after which time it was analyzed by GC and $^1$H NMR.

The invention claimed is:

1. A N-heterocyclic carbene (NHC) ligand comprising cis- or trans-isomers of the compound of formula (1) or a salt thereof:

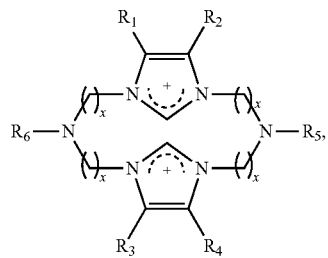

(I)

wherein:
$R_1$ and $R_2$ are each, individually, hydrogen, a substituted or unsubstituted C1 to C10 hydrocarbyl group, or $R_1$ and $R_2$ together form a saturated or unsaturated C3 to C10 ring;

$R_3$ and $R_4$ are each, individually, hydrogen, a substituted or unsubstituted C1 to C10 hydrocarbyl group, or $R_3$ and $R_4$ together form a saturated or unsaturated C3 to C10 ring;

$R_5$ and $R_6$ are substituted or unsubstituted C1 to C10 hydrocarbyl groups; and x is an integer from 1 to 6, and wherein cis or trans refers to the relationship of $NR_5$ and $NR_6$.

2. The ligand of claim 1, wherein $R_1$, $R_2$, $R_3$, and $R_4$ are each hydrogen, forming a compound of Formula (II):

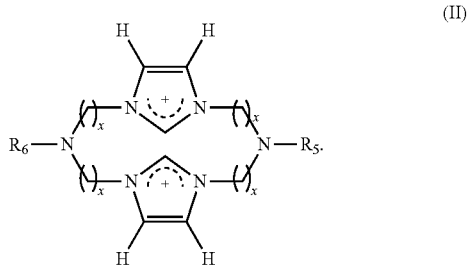

(II)

3. The ligand of claim 1, wherein $R_5$ and $R_6$ are both benzyl $CH_2C_6H_5$ groups.

4. The ligand of claim 1, wherein the composition comprises a salt and the salt is a halide salt.

5. The ligand of claim 1, wherein the composition comprises a trans isomer.

6. The ligand of claim 1, wherein $R_1$, $R_2$, $R_3$, and $R_4$ are each hydrogen, and $R_5$ and $R_6$ are each benzyl $CH_2C_6H_5$ group, and the ligand is the trans-isomer.

* * * * *